US005739303A

United States Patent [19]
Beck et al.

[11] Patent Number: 5,739,303
[45] Date of Patent: Apr. 14, 1998

[54] METHOD FOR DECARBONYLATION OF SUGARS

[75] Inventors: Roland Herwig Friedrich Beck, Everberg; Myriam Elseviers, Kampenhout; Hilde Odile Jozefine Lemmens, Kontich, all of Belgium

[73] Assignee: Cerestar Holding B.V., Sas Van Gent, Netherlands

[21] Appl. No.: 567,701

[22] Filed: Dec. 5, 1995

[30] Foreign Application Priority Data

Dec. 6, 1994 [GB] United Kingdom ............... 9424566

[51] Int. Cl.$^6$ .................... C07C 29/14; C07H 1/00
[52] U.S. Cl. .................... 536/18.5; 536/1.11; 536/124; 568/863
[58] Field of Search .................... 536/1.11, 18.5, 536/124, 125; 568/852, 861, 862, 863

[56] References Cited

U.S. PATENT DOCUMENTS

| H918 | 5/1991 | Andrews et al. | 549/497 |
| 3,948,965 | 4/1976 | Cawse | 260/449 R |

OTHER PUBLICATIONS

Journal of Organic Chemistry, vol. 54, No. 22, 27 Oct. 1989, Washington, DC, US, pp. 5257–5264, M.A. Andrews et al "decarbonylation of unprotected aldose sugars by chlorotris–(triphenylphosphine) rhodium (I). A new descent of series approach to alditols".

Collins & Ferrier, Monosaccharides—Their Chemistry and Their Roles in Natural Products, (John Wiley & Sons), p. 4, (1995).

Primary Examiner—John Kight
Assistant Examiner—Howard C. Lee
Attorney, Agent, or Firm—Cushman, Darby & Cushman IP Group of Pillsbury Madison & Sutro LLP

[57] ABSTRACT

The present invention discloses a method for direct decarbonylation of sugars. The method is based on the conversion of the sugars in the presence of a phosphine metal complex. These complexes are added in catalytic amounts if at the same time urea or an azide such as DPPA (diphenylphosphorylazide) or sodium azide is added. Through the use of other ligands the decarbonylation reaction can also be performed in water.

18 Claims, 1 Drawing Sheet

METHOD FOR DECARBONYLATION OF SUGARS

TECHNICAL FIELD

The present invention discloses a method for producing polyols from sugars characterized in that the sugar is decarbonylated. Specifically, the present invention discloses a method for catalytic decarbonylation of unprotected aldose sugars. In general terms Cn aldose sugars are converted to Cn-1 alditols. The method of the present invention is illustrated by the catalytic decarbonylation of glucose to arabinitol which is used for the preparation of xylitol.

BACKGROUND OF THE INVENTION

Andrews et at. J. Org. Chem. (1989) 54 5257-5264 describe the decarbonylation of unprotected aldose sugars by chlorotris(triphenylphosphine)rhodium(I). Unprotected Cn aldose sugars are cleanly decarbonylated by 1 equivalent of chlorotris(triphenylphosphine)rhodium(I) in 1-24 h at 130° C. in N-methyl-2-pyrrolidinone solution to give the corresponding Cn-1 alditol. According to the authors attempts to make the reactions catalytic have not been very successful. No details relating to these attempts are reported. Large scale application of this method, involving the use of large amounts of rhodium is therefore not feasible.

In US Statutory Invention Registration No. H918 M. A. Andrews and S. A. Klaeren describe the simultaneous dehydrogenation and decarbonylation of alcohols. Primary alcohols including sugar alditols are simultaneously dehydrogenated and decarbonylated by heating a mixture of rhodium and ruthenium complexes, the alcohol and optionally a hydrogen acceptor, in an acceptable solvent. Again stoichiometric amounts of the metal complexes are used.

Application of these decarbonylation reactions is further limited by the solvents used. The preferred solvents are polar enough to dissolve the sugar however they should be sufficiently non-coordinating to permit the metal complexes to function effectively. These characteristics have limited the solvents which can be used with the indicated metal complexes. Water, which would be the preferred solvent for large scale sugar conversion applications, can not be used with the metal complexes used by Andrews et al.

In principle the indicated decarbonylation and dehydrogenation/decarbonylation reactions can be used to convert any Cn aldose or Cn alditol sugars to the corresponding Cn-1 alditols.

At present industrial production of pentitols is mainly restricted to production of xylitol. Xylitol is produced in four steps:

xylose containing plant material is acid hydrolysed, the hydrolysate is purified to either a pure xylose solution or a pure crystalline xylose, the xylose is hydrogenated to xylitol, the xylitol is crystallized.

Drawbacks of this method are the low overall yield and the low product purity. Extensive purification has to be performed i.e. ion-exchange treatment to remove the acid used for hydrolysis and color formed during hydrolysis, and crystallization to remove the hemicellulosic sugars also formed during hydrolysis.

All recently published methods to produce xylitol start from readily available hexoses, in particular D-glucose, D-galactose and D-fructose or L-sorbose. In a first reaction step the hexose is submitted to a chain shortening reaction which yields a $C_5$-intermediate. The second basic reaction step (which might be actually more than one step) is the conversion of the $C^5$-intermediate into xylitol.

In European patent applications EP 403 392 and EP 421 882 (both Roquette Frères SA) a process is disclosed in which glucose is fermented to D-arabinitol by an osmophilic yeast, the arabinitol ($C_5$-intermediate) is then converted by bacteria (Acetobacter, Gluconobacter or Klebsiella) into D-xylulose. The xylulose is further isomerised by glucose (xylose) isomerase into a xylose/xylulose mixture. This mixture is either directly hydrogenated to xylitol or the xylose is enriched prior to hydrogenation.

International patent application WO 93/19030 (Amylum) discloses how glucose, fructose, galactose or mixtures thereof (obtained by hydrolysis of the disaccharides sucrose and lactose) are oxidatively decarboxylated into alkali arabinonate and lyxonate, respectively. These aldonic acids are the $C_5$-intermediates, which are transformed into xylitol via arabinitol (=lyxitol). When L-sorbose is used in this sequence L-xylonate is obtained, which is directly hydrogenated to xylitol.

The chain shortening steps in these published methods for producing xylitol are fermentation and oxidative decarboxylation, in none of the recently published methods for xylitol production mention is made of the use of a decarbonylation step.

Other well known chemical methods for xylitol production include protection group chemistry. These methods can not be economically applied on a large scale therefore they are not considered in detail (Helv.Chim.Acta 58, 1975, 311).

Several purely microbiological pathways have been published. However none of them seems economically interesting because overall yield is too low.

There exists therefore a need for a method of producing pentitols such as xylitol in a high yield and with a reduced level of impurities. The present invention provides such a method.

SUMMARY OF THE INVENTION

The present invention provides a method for producing a polyol from a sugar characterized in that the sugar is decarbonylated in the presence of phosphine metal complexes yielding a polyol. The phosphine metal complex can be selected from the group comprising tri-aryl phosphine metal complexes comprising phenyl and substituted phenyl phosphine metal complexes and bis(diphenylphosphino)alkane metal complexes.

Specifically, the invention provides a method for production of a polyol from a sugar wherein the sugar is selected from the group consisting of $C_6$-sugars, $C_5$-sugars, deoxy ($C_6$ and $C_5$) sugars and aminosugars and characterized in that the phosphine metal complexes are used in catalytic amounts. Catalytic amounts of phosphine metal complex can be used upon addition of azides such as diphenylphosphorylazide or sodium azide, urea or ammonia to the reaction mixture.

bis(diphenylphosphino)alkane metal complexes are used in catalytic amounts without the addition of the mentioned azides, urea or ammonia.

The present invention further provides a method for producing a pentitol from a hexose characterized in that the hexose is decarbonylated in the presence of phosphine metal complexes to yield a pentitol. Specifically, glucose is converted to arabinitol in the presence of catalytic amounts of phosphine metal complexes.

The present invention further discloses pentitols produced according to the direct decarbonylation method. The pentitols obtained with the method of the present invention are optionally treated further i.e. isomerization and purification. In the case of arabinitol this leads to xylitol.

The invention discloses the use of group 8 metals and copper in the phosphine metal complexes. The present invention further discloses that catalytic amounts of azides such as DPPA or sodium azide, urea or ammonia can be used in combination with catalytic amounts of phosphine metal complex.

In another aspect of the invention it is shown that catalytic amounts of the phosphine metal complex can also be used when the metal contains bis(diphenylphosphino) alkane ligands in which case the addition of azides, urea or ammonia is not required.

The present invention also shows that the decarbonylation reaction can be performed in water upon use of triphenyl phosphinetrisulfonic acid (TPPTS) together with added triphenylphosphine.

In yet another aspect of the invention it is shown that the triphenylphosphine can be used in a polymer bound form. This facilitates the recovery and reuse of the triphenylphosphine and also the purification of the product of the decarbonylation reaction.

DETAILED DESCRIPTION OF THE INVENTION

Figure 1:
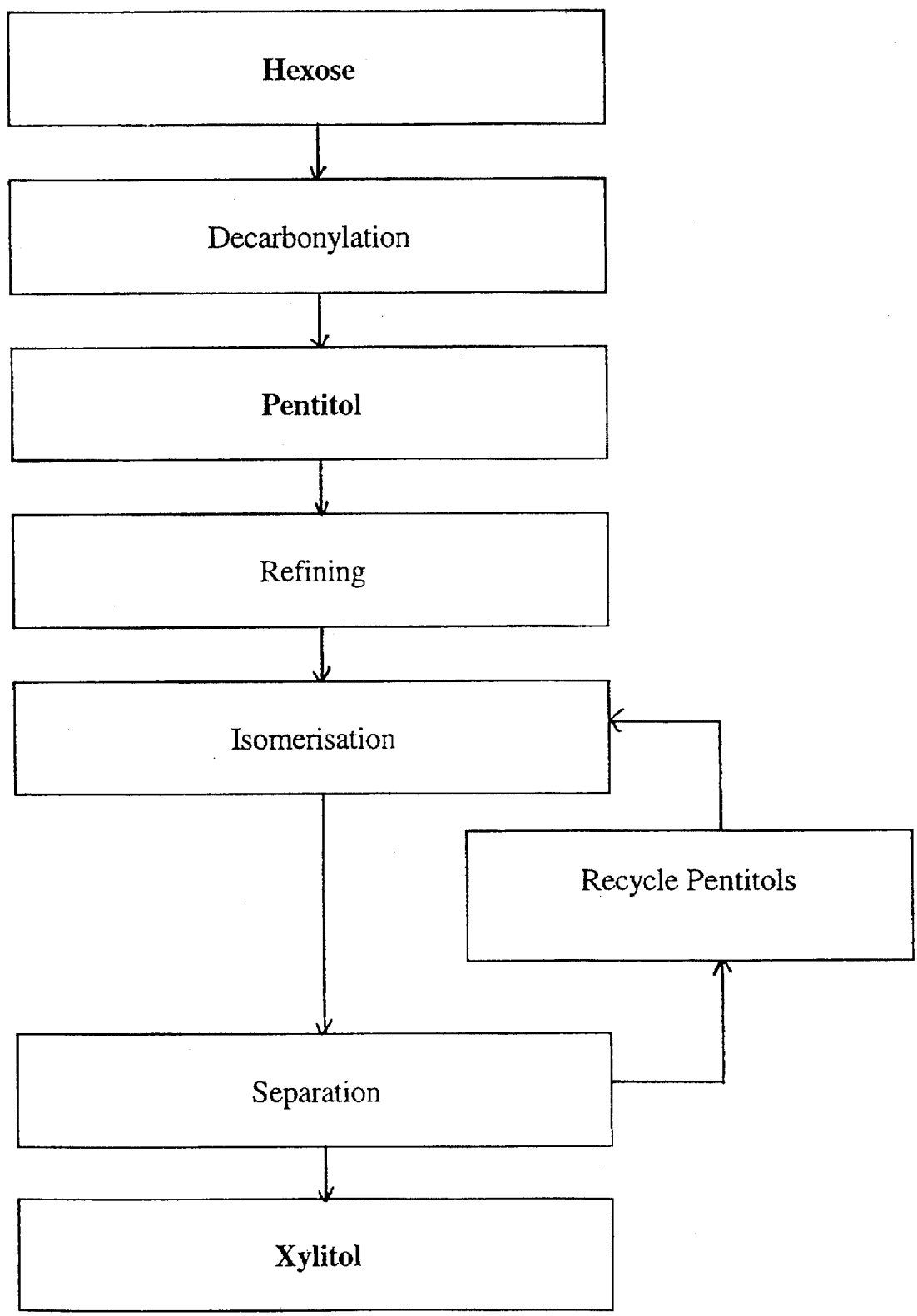

The present invention provides a method for producing a polyol from a sugar characterized in that the sugar is decarbonylated in the presence of phosphine metal complexes yielding a polyol. In the most general form the invention provides a method for production of a polyol from a sugar wherein the sugar is selected from the group consisting of $C_6$-sugars, $C_5$-sugars, deoxy ($C_6$ and $C_5$) sugars and aminosugars and wherein the reaction is characterized in that the phosphine metal complexes are used in catalytic amounts. Catalytic amounts of phosphine metal complex can be used upon addition of azides such as diphenylphosphorylazide or sodium azide, urea or ammonia to the reaction mixture.

Sugars which are suitably employed in the reactions according to the present invention and which give the indicated products are mentioned in Table I

TABLE I

Non-exhaustive list of sugars which can be decarbonylated according to the subject invention

| | product |
|---|---|
| $C_6$ sugars | |
| glucose | |
| mannose | arabinitol |
| allose | |
| altrose | ribitol |
| gulose | |
| idose | xylitol |
| galactose | |
| talose | lyxitol (=arabinitol) |
| $C_5$ sugars | |
| ribose | |
| arabinose | erythritol |
| xylose | |
| lyxose | threitol |

Deoxysugars such as, 2-deoxyglucose, 2-deoxyribose, fucose and rhamnose and aminosugars such as glucosamine and N-acetylglucosamine can likewise be used in the present reaction. The present invention further provides a method for producing a pentitol from a hexose characterized in that the hexose is decarbonylated in the presence of phosphine metal complexes to yield a pentitol. Specifically, glucose is converted to arabinitol in the presence of catalytic amounts of phosphine metal complexes.

In a typical reaction glucose is dissolved in a solvent e.g. N-methyl-2-pyrrolidinone, the complex is added. The solution is purged with nitrogen gas. The vessel is sealed and brought to the desired reaction temperature i.e. between room temperature and 130° C. The reaction is stopped after completion of the decarbonylation.

The decarbonylation method of the present invention is based on the use of a phosphine based metal complex as a catalyst (Example 1). The invention discloses the use of group 8 metals and copper in the phosphine metal complexes (Example 2). The triphenylphosphine metal complexes are prepared as described for example in J. Org. Chem. 1989, 54, 5257–5264. The present invention discloses the use of $Rh^{3+}$, $Rh^{1+}$, $Ru^{2+}$, $Ni^{2+}$, $Fe^{2+}$, $Co^{2+}$ and $Cu^{1+}$ as metal ions. The preferred metal ions are $Rh^{3+}$, $Co^{2+}$, $Rh^{1+}$ and $Ni^{2+}$ these ions are preferred for giving the highest pentitol yield.

In the presence of rhodium the reaction can be easily visually monitored. The deep red starting color of the tris(triphenylphosphine) rhodium (I) chloride complex gradually lightens, becomes orange and then bright yellow in a titration-like step due to carbonyl chlorobis (triphenylphosphine) rhodium (I).

Through the addition of completing agents e.g. azides such as diphenylphosphonylazide (DPPA) and sodium azide, urea or ammonia the consumption of the metal complexes is reduced to catalytic amounts instead of stoichiometric amounts (Examples 5, 7 and 8). Cationic complexes with chelating diphosphine ligands instead of the usual triphenylphosphine complex allow catalytic addition of the complex. Replacing one of the triphenylphosphine ligands by a polymer bound triphenylphosphine ligand allows easy recuperation of the complex.

The present invention further discloses that catalytic amounts of azides such as DPPA, or sodium azide and urea (Example 8) can be used in combination with catalytic amounts of phosphine metal complex.

The molar ratio of hexose to triphenylphosphine metal complex is from 1:3 to 40:1.

The preferred solvent is N-methyl-2-pyrrolidinone. It is also demonstrated that by changing the triphenylphosphine ligand to a more water soluble ligand the reaction can be performed in water. Other solvents may also be used as mixtures of water and solvent.

The present invention shows that the decarbonylation reaction can be performed in water upon use of triphenyl phosphinetrisulfonic acid (TPPTS) together with added triphenylphosphine (Example 3 and 4).

Replacing one of the triphenylphosphine ligands by a polymer bound triphenylphosphine ligand allows easy recuperation of the complex.

When glucose is used as starting hexose the reaction product is found to contain arabinitol, isomerized hexoses and hexitols and unreacted glucose.

The relative amount of arabinitol formed in the decarbonylation product is preferably larger than 20% more preferably larger than 40%.

It is further shown that large scale arabinitol production is possible with the method of the subject invention.

The present invention discloses the direct decarbonylation of $C_6$-sugars which results in $C_5$-polyols. Starting with glucose the decarbonylation yields arabinitol. To obtain xylitol the arabinitol is isomerized by methods known in the art. These methods include treatment with hydrogenation/dehydrogenation catalysts at elevated temperatures and pressures in the presence of alkali or acids and hydrogen. The mixture of pentitols obtained is subjected to chromatography on cationic resin material yielding purified xylitol.

Xylitol can be separated from the reaction product mixture by chromatography as described for example in Chem. Zvesti 34 (1980) 530. Preferably the mixture is first demineralized and subsequently submitted to chromatography. The refining is suitably performed using a strong cation exchanger resin e.g. Duolite C 26 followed by a medium base anion exchange resin Duolite A 368. Preferably this process is repeated. On a larger scale chromatography is performed using suitable equipment for example obtainable from Mitsubishi with equipped Diaion UBK-555 resin (in $Ca^{2+}$ form). Separation methods have been described for example in EP 0 403 392, and the references cited therein (page 5 line 39 —page 6 line 21).

Application of the method of the present invention to the production of xylitol is schematically represented in FIG. 1.

The method for producing xylitol according to the present invention is characterized in that the starting sugar is glucose, the decarbonylation product is arabinitol, the arabinitol is converted to xylitol by catalytic isomerization or enzymatic isomerization, the xylitol is further purified through chromatography, optionally the xylitol is crystallized.

The advantage of the method of the present invention is the reaction steps and the higher yield compared with the oxidative decarboxylation reaction disclosed in WO 93/19030 and with the fermentative decarboxylation described in EP 403 392 and EP 421 882.

The present invention discloses the following improvements over the existing decarbonylation.

Example 1 describes the standard process wherein the tris(triphenylphosphine) rhodium (I) chloride is used in an equimolar amount with glucose.

Instead of the known rhodium complex other group 8 metals are used, this is shown in example 2, 8 and 11.

Examples 3 and 4 disclose that by addition of the sulfonic acid groups to the phosphine ligands the phosphine complex can be used in water.

Example 7 shows that when DPPA or sodium azide are added in equimolar amounts the phosphine metal complex can be used in catalytic amounts.

Example 5 discloses that the addition of DPPA in catalytic amounts with respect to glucose makes possible the catalytic addition of the phosphine metal complex, the same is shown for the addition of urea and sodium azide in example 8. Example 5 also shows how the arabinitol is further converted to xylitol. The arabinitol produced in the other examples can likewise be converted to xylitol.

Examples 9, 10 and 11 show that catalytic amounts of the phosphine metal complex can also be used when bis (diphenylphosphino) alkane ligand are used. Alkanes in this case are selected from C1 to C10, preferably C1 to C6.

Example 12 shows that triphenylphosphine is used in polymer bound form.

The invention is further illustrated by the following detailed examples.

EXAMPLES

Example 1

1.935 g glucose was dissolved in 50 g N-methyl-2-pyrrolidinone. 9.95 g of tris-(triphenylphosphine) rhodium (I) chloride (prepared as described in J. Org. Chem., 1989 54 5257–5264) was added to the glucose solution. This corresponds to a molar ratio of 1:1 between the glucose and the triphenylphosphine metal complex. The solution was purged with nitrogen gas for 2 minutes, the reaction vessel sealed and brought to a temperature of 130° C. The reaction was terminated when the deep red color of the rhodium triphenylphosphine complex disappeared and the yellow color of the rhodium carbonyl triphenylphosphine complex appeared (approx. 8 hours).

The product had the following composition (HPLC analysis): 74% D-arabinitol, 20% unreacted glucose, 2% isomerized hexoses (fructose and mannose), 1% glycerol and 3% unidentified products.

Example 2

Performed as Example 1, with the exception that other group 8 metal triphenylphosphine complexes were used. Reaction conditions were the same, but additionally triphenylphosphine (TPP) was added where indicated.

| Metal | Ru | Ru | Ni | Ni | Ni | Co(I) | Co(II) | Co(II) | Cu(I) |
|---|---|---|---|---|---|---|---|---|---|
| [Metal]:[TPP] | 1:3 | 1:3 | 1:2 | 1:2 | 1:2 | 1:3 | 1:2 | 1:2 | 1:3 |
| ratio free [TPP]:[glucose] | 1:1 | 3:1 | 0 | 1:1 | 2:1 | 0 | 0 | 2:1 | 1:1 |
| Arabinitol [%] | 38 | 44 | 27 | 36 | 50 | 50 | 61 | 66 | 9 |
| Isomerized hexoses [%] | 8 | 6 | 26 | 15 | 14 | 8 | 6 | 8 | 9 |
| Sorbitol [%] | 30 | 27 | 14 | 7 | 4 | 9 | 3 | 2 | 1 |
| Unreacted glucose [%] | 22 | 22 | 29 | 40 | 30 | 16 | 30 | 23 | 80 |
| Glycerol [%] | 2 | 1 | 4 | 2 | 2 | 17 | 0 | 1 | 1 |

Example 3

1.935 g glucose was dissolved in 50 g demineralized water. 2.83 g of rhodium trichloride trihydrate and 18.33 g triphenyl phosphinetrisulfonic acid (TPPTS) was added to the glucose solution. This corresponds to a molar ratio of 1:1 between glucose and rhodium complex and a molar ratio of 3:1 between TPPTS and rhodium. The solution was purged with nitrogen gas for 2 minutes, the reaction vessel sealed and brought to a temperature of 100° C. The reaction time was 8 hours. For comparison reasons a reaction of glucose in N-methyl-2-pyrrolidinone (NMP) using the tris (triphenylphosphine)rhodium(I) chloride (as in example 1) at 100° C. is included here.

| Metal | $Rh^{+++}$ | $Rh^+$ |
|---|---|---|
| [Metal]:[Phosphine] | 1:3 | 1:3 |
| Solvent | water | NMP |
| Arabinitol [%] | 19 | 46 |
| Isomerized hexoses [%] | 2 | 2 |
| Unreacted glucose [%] | 52 | 37 |

Example 4

1.935 g glucose was dissolved in 50 g demineralized water. 2.83 g rhodium trichloride trihydrate and 18.33 g triphenyl phosphinetrisulfonic acid (TPPTS) was added to the glucose solution followed by 2.82 g triphenylphosphine to reduce rhodium(III) to rhodium(I). This corresponds to a molar ratio of 1:1 between glucose and rhodium complex and a molar ratio of 3:1 between TPPTS and rhodium, and a molar ratio of 1:1 between TPP and glucose. The solution was purged with nitrogen gas for 2 minutes, the reaction vessel sealed and brought to a temperature of 130° C. The reaction time was 24 hours.

The product had the following composition (HPLC analysis): 53% arabinitol, 25% unreacted glucose, 17% isomerized hexoses (being mannose+fructose), and 5% sorbitol.

Example 5

38.8 g glucose was dissolved in 500 g N-methyl-2-pyrrolidinone. 10 g of tris(triphenylphosphine)rhodium(I) chloride (prepared as described in J. Org. Chem., 1989 54 5257-5264) and 3.7 g diphenylphosphorylazide (DPPA) were added to the glucose solution. This corresponds to a molar ratio of 20:1 between the glucose and the triphenylphosphine metal complex and a molar ratio of 100:6.25 between the glucose and DPPA. The solution was purged with nitrogen for 2 minutes, the reaction vessel sealed and kept for 24 hours at 50° C. After cooling down the reaction mixture to room temperature, the reaction mixture was extracted with 1 L chloroform and 500 ml water. The water-phase was again twice extracted with 500 ml of chloroform. The water-phase was evaporated until all residual N-methyl-2-pyrrolidinone was removed. The obtained syrup had the following composition (HPLC-analysis):

Arabinitol [%]: 49

Residual glucose [%]: 49

Isomerized hexoses [%]: 1

Reduced hexoses [%]: 1

The arabinitol was separated from the other sugar fraction by using chromatography with Diaion UBK-555 resin in the $Ca^{++}$-form. 97% (purity 99%) of the arabinitol fraction was recuperated. The obtained arabinitol syrup was isomerized on a ruthenium catalyst (2% catalyst on total dry substance), which was supported on active carbon (5% Ru on carbon). To the syrup phosphoric acid (1.5% on total dry substance) was added. The reaction temperature was 150° C. at a hydrogen pressure of 4 MPa. Within 5 hours the isomerization had proceeded to a sufficient level, containing 95% total pentitols (of which 29% xylitol, 16% ribitol and 55% D,L-arabinitol) and 5% tetritols and triitols.

The xylitol was further purified through chromatography on cation exchange resin in the calcium form yielding xylitol with a purity of greater than 95%. The other products were recycled to the isomerization step. The purified xylitol was crystallized.

Example 6

Performed as example 5, with the exception that other group 8 metal triphenylphosphine complexes were used. Reaction conditions were the same.

| Metal | Rh | Rh | Ru |
|---|---|---|---|
| [Metal]:[TPP] | 1:3 | 1:3 | 1:3 |
| ratio free [TPP]:[glucose] | 0 | 0 | 7.5:100 |
| ratio [glucose]:[complex] | 100:5 | 100:2.5 | 100:2.5 |
| ratio [DPPA]: [glucose] | 6.25:100 | 6.25:100 | 6.25:100 |
| Arabinitol [%] | 49 | 46 | 40 |
| Isomerised hexoses [%] | 1 | 1 | 10 |
| Sorbitol [%] | 1 | 0 | 0 |
| Unreacted Glucose [%] | 49 | 54 | 44 |
| Glycerol [%] | 0 | 0 | 6 |

Example 7

1.94 g glucose was dissolved in 50 g N-methyl-2-pyrrolidinone. 0.5g of chlorotris(triphenylphosphine) rhodium(I) (prepared as described in J. Org. Chem.,1989 54 5257-5264) and 0.70 g sodium azide were added to the glucose solution. This corresponds to a molar ratio of 20:1 between the glucose and the triphenylphosphine metal complex and a molar of 1:1 between the glucose and sodium azide. The solution was purged with nitrogen for 2 minutes, the reaction vessel sealed and kept for 48 hours at room temperature. For comparison reasons a reaction of glucose using equimolar amounts of DPPA is included here.

The product had the following composition (HPLC-analysis)

| Addition equimolar: | $NaN_3$ | DPPA |
|---|---|---|
| Arabinitol [%]: | 45 | 25 |
| Residual glucose [%]: | 49 | 75 |
| Isomerized hexoses [%]: | 6 | 0 |

Example 8

1.94 g glucose was dissolved in 50 g N-methyl-2-pyrrolidinone. 0.5 g of triphenylphosphine metal complex and catalytic amounts of sodium azide or urea were added to the glucose solution. This corresponds to a molar ratio of 20:1 or 40:1 between the glucose and the triphenylphosphine metal complex and a molar ratio of 100:6.25 between the glucose and sodium azide or urea. The solution was purged with nitrogen for 2 minutes, the reaction vessel sealed and kept for 24 hours at 50° C.

The product had the following composition (HPLC-analysis):

| Metal | Rh | Rh | Ni | Co |
|---|---|---|---|---|
| [Metal]:[TPP] | 1:3 | 1:3 | 1:2 | 1:2 |
| ratio free [TPP]:[glucose] | 0 | 0 | 10:100 | 10:100 |
| ratio [glucose]:[complex] | 100:5 | 100:2.5 | 100:5 | 100:5 |
| ligand | $NaN_3$ | urea | urea | urea |
| ratio [ligand]:[glucose] | 6.25:100 | 6.25:100 | 6.25:100 | 6.25:100 |
| Arabinitol [%] | 47 | 52 | 21 | 20 |
| Isomerized hexoses [%] | 2 | 0 | 4 | 4 |
| Sorbitol [%] | 2 | 3 | 11 | 10 |
| Unreacted Glucose [%] | 49 | 45 | 64 | 65 |
| Glycerol [%] | 0 | 0 | 0 | 1 |

Example 9

1.91 g chlorocarbonylbis(triphenylphosphine)rhodium(I) was added to 50 g N-methyl-2-pyrrolidinone and the mixture was stirred at 80° C. for 15 minutes. 2.61 g 1,4-bis-(diphenylphosphino) butane was added to the solution and stirred at 80° C for 1 hour. 5 g glucose was added. This corresponds to a molar ratio of 10:1 between the glucose and the metal complex. The solution was purged with nitrogen gas for 2 minutes, the reaction vessel sealed and brought to a temperature of 130° C. for 24 hours.

The product had the following composition (HPLC-analysis)

Arabinitol [%]: 30

Residual glucose [%]: 62

Isomerized pentitols [%]: 0

Isomerized hexoses [%]: 3

Reduced hexoses→hexitols [%]: 3

Degraded products (e.g. glycerol): 2

Example 10

0.96 g chlorocarbonylbis(triphenylphosphine)rhodium(I) was added to 50 g N-methyl-2-pyrrolidinone and the mixture was stirred at 80° C. for 15 minutes. 1.39 g 1,6-bis-(diphenylphosphino)hexane was added to the solution and stirred at 80° C for 1 hour. 5 g glucose was added, followed by 0.73 g triphenylphosphine. This corresponds to a molar ratio of 20:1 between the glucose and the metal complex and a molar ratio of 10:1 between glucose and TPP. The solution was purged with nitrogen gas for 2 minutes, the reaction vessel sealed and brought to a temperature of 130° C. for 24 hours.

The product had the following composition (HPLC-analysis)

Arabinitol [%]: 47
Residual glucose [%]: 44
Isomerized pentitols [%]: 0
Isomerized hexoses [%]: 1
Reduced hexoses→hexitols [%]: 0
Polymerized products: 8

Example 11

Performed as example 9 with the exception that other group 8 metal complexes were used. As chelating ligand 1,2-bis-(diphenylphosphino)ethane (BPPE) was used. The product had the following composition (HPLC-analysis)

| Metal | Rh | Rh | Ni | Fe |
|---|---|---|---|---|
| [Metal]:[BPPE] | 1:2 | 1:2 | 1:2 | 1:2 |
| ratio [glucose]:[complex] | 100:10 | 100:10 | 100:10 | 100:5 |
| Addition of free TPP | − | + | − | + |
| ratio [glucose]:[TPP] |  | 10:1 |  | 10:1 |
| Arabinitol [%] | 30 | 31 | 55 | 8 |
| Isomerized hexoses [%] | 9 | 3 | 12 | 4 |
| Sorbitol [%] | 6 | 7 | 3 | 2 |
| Unreacted Glucose [%] | 54 | 56 | 29 | 85 |
| Polymerized products [%] | 1 | 3 | 1 | 1 |

Example 12

1.935 g glucose was dissolved in 50 g N-methyl-2-pyrrolidinone. 2.83 g rhodium trichloride trihydrate and 8.45 g triphenylphosphine and 4.25 g triphenylphosphine polymer bound (3 mmol TPP/resin, copolymer of 98% styrene and 2% divinylbenzene, diphenylphosphinated) were added to the glucose solution. This corresponds to a molar ratio of 1:1 between the glucose and the triphenylphosphine metal complex. The solution was purged with nitrogen gas for 2 minutes, the reaction vessel sealed and brought to a temperature of 130° C. The reaction time was 24 hours.

The product had the following composition (HPLC analysis): 20% D-arabinitol, 26% unreacted glucose, 30% isomerized hexoses (fructose and mannose), 1% glycerol and 23% sorbitol.

We claim:

1. A method for catalytically producing a polyol from an aldose comprising decarbonylating the aldose in the presence of a catalytic amount of a phosphine metal complex, wherein the ratio of said aldose to said phosphine metal complex is at least 10 to 1.

2. A method according to claim 1 wherein the phosphine metal complex is a triaryl phosphine metal complex or a bis(diphenylphosphino)alkane metal complex.

3. A method according to claim 2 wherein the phosphine is selected from the group consisting of triphenyl phosphine, triphenyl-phosphine trisulfonic acid and bis (diphenylphosphino)alkane wherein the alkane has from 1 to 10 C-atoms.

4. A method according to claim 1 wherein the aldose is selected from the group consisting of $C_6$-aldoses, $C_5$-aldoses, deoxy ($C_6$ and $C_5$) aldoses and aminoaldoses.

5. A method according to any one of claims 1 to 4, in which the decarbonylation is performed in the presence of a catalytic amount of a phosphine metal complex wherein the ratio of said aldose to said phosphine metal complex is at least 10 to 1, and a compound selected from the group consisting of an azide, urea and ammonia.

6. A method according to claim 5 wherein the decarbonylation is performed in the presence of a catalytic amount of a compound selected from the group consisting of an azide, urea and ammonia, and wherein the ratio of said aldose to said compound is at least 10 to 1.

7. A method for the decarbonylation of aldoses, which comprises decarbonylating the aldose in the presence of a phenylphosphine metal complex in water.

8. A method for the decarbonylation of aldoses according to claim 7 wherein the aldose is decarbonylated in the presence of a triphenyl phosphinetrisulfonic acid (TPPTS) in water.

9. A method according to claim 7 or 8 wherein when rhodium is used as the metal cation in the phenylphosphine metal complex, triphenylphosphine is added.

10. A method for the catalytic decarbonylation of aldoses, which comprises decarbonylating the aldose in the presence of a polymer bound phenyl phosphine metal complex.

11. A method according to claim 10 wherein the polymer is a copolymer of styrene and divinylbenzene.

12. A method according to any one of claims 1, 7, or 10, wherein the metal in the metal complex is a metal cation which is $Ni^{2+}$, $Rh^{3+}$, $Rh^{1+}$, $Ru^{2+}$, $Fe^{2+}$, $Co^{2+}$ or $Cu^{1+}$.

13. A method according to any one of claims 1, 7, or 10, wherein the aldose is glucose, the product of decarbonylating the aldose is arabinitol, and, wherein the method further comprises the steps of converting the arabinitol to xylitol by catalytic isomerization or enzymatic isomerization, and purifying the xylitol by chromatography.

14. A method according to claim 3, wherein the alkane has from 1 to 6 C atoms.

15. A method according to claim 5, wherein said azide is diphenylphosphorylazide or sodium azide.

16. A method according to claim 6, where said azide is diphenylphosphorylazide or sodium azide.

17. A method according to claim 12, wherein the metal cation is $Rh^{3+}$, $Co^{2+}$, $Rh^{1+}$ or $Ni^{2+}$.

18. A method according to claim 13, wherein the xylitol is crystallized.

* * * * *